United States Patent [19]

Banerjee et al.

[11] 4,403,503

[45] Sep. 13, 1983

[54] APPARATUS AND METHOD FOR THE REDUCTION OF INTERFERENCES IN CHROMATOGRAPHY

[76] Inventors: Sujit Banerjee, 128 E. Remington Ave., Syracuse, N.Y. 13210; Edward J. Pack, Jr., Cobblestone Sq., Clay, N.Y. 13041

[21] Appl. No.: 319,260

[22] Filed: Nov. 9, 1981

[51] Int. Cl.³ .......................................... G01N 31/08
[52] U.S. Cl. ................................. 73/61.1 C; 73/23.1; 210/198.2; 422/70
[58] Field of Search ........................ 73/61.1 C, 23.1; 210/198.2, 656; 422/70

[56] References Cited

U.S. PATENT DOCUMENTS

| 3,508,880 | 4/1970 | Hrdina | 73/61.1 C X |
| 3,847,550 | 11/1974 | Scott et al. | 73/61.1 C X |
| 3,981,179 | 9/1976 | Roof | 73/61.1 C |
| 4,032,445 | 6/1977 | Munk | 73/61.1 C X |
| 4,043,906 | 8/1977 | Helmer | 73/61.1 C X |
| 4,070,284 | 1/1978 | Fujita et al. | 210/198.2 X |
| 4,137,161 | 1/1979 | Shimada et al. | 210/198.2 X |

Primary Examiner—E. R. Kazenske
Assistant Examiner—Joseph W. Roskos
Attorney, Agent, or Firm—Bruns & Jenney

[57] ABSTRACT

Apparatus and method for improving the definition of a signal of interest in the presence of certain types of interfering signals in chromatography. The apparatus in one embodiment of the invention includes a chromatographic column through which a sample can be passed and a first detector, a variable volume cell and a second detector connected in series with the first detector being connected to the output of the column. The apparatus also includes a device for recording the differential output of the detectors. By passing the sample sequentially through the detectors and adjusting the volume of the variable volume cell, the interfering components can be made to be present in both detectors whereby partial cancellation occurs and the signal of interest becomes more readily detectable. In another embodiment of the invention, where detection is accompanied by destruction of the sample, a device is provided to split the outflow of the column and one resultant portion of the outflow goes directly to a first detector and the other portion goes to a variable volume cell and a second detector connected in series.

12 Claims, 11 Drawing Figures

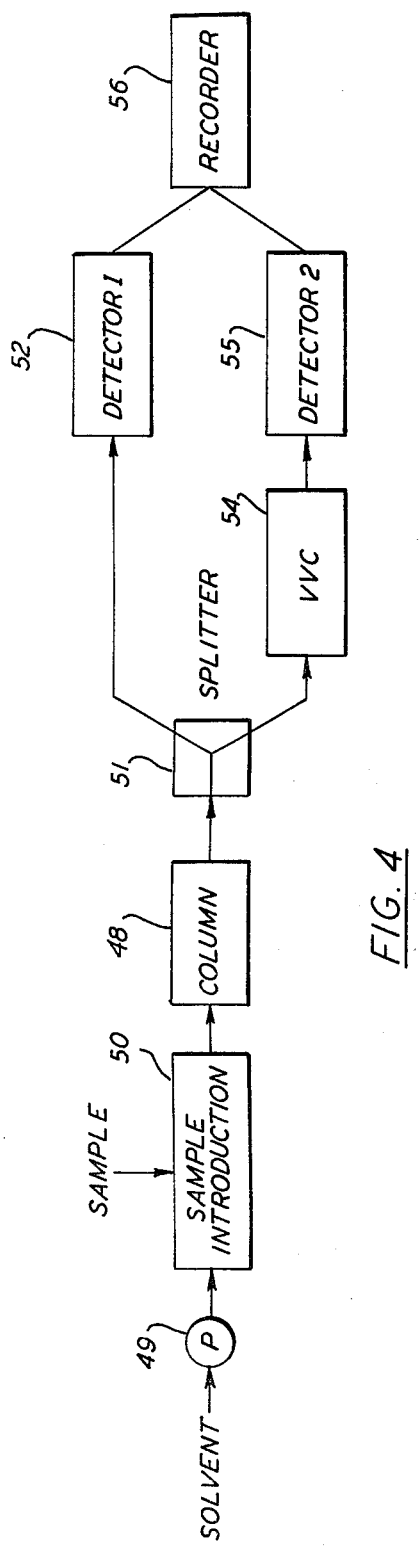
FIG. 4
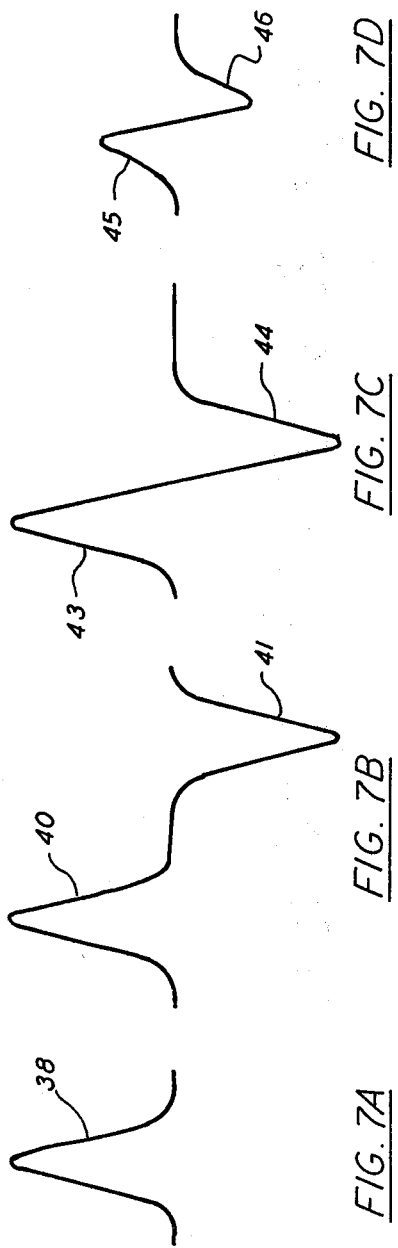
FIG. 7A
FIG. 7B
FIG. 7C
FIG. 7D

APPARATUS AND METHOD FOR THE REDUCTION OF INTERFERENCES IN CHROMATOGRAPHY

BACKGROUND OF THE INVENTION

This invention relates generally to chromatography, and has particular reference to a novel apparatus and method for reducing interferences in chromatography.

The quantitation of components in a complex mixture by chromatography is frequently limited by the presence of interfering signals which are caused by components in the mixture having similar characteristics to components that are producing signals of interest. The problem is particularly accute when the complex mixtures are of biological or environmental origin, and elaborate clean-up and/or derivatization methods are often required for these analyses.

The applicants are not aware of any prior art that has addressed itself to the problem of reducing or minimizing interfering signals in chromatography through difference methods. The closest prior art known to the applicants is U.S. Pat. No. 3,847,550, issued Nov. 12, 1974 to Charles D. Scott et al. This patent is directed to a method of carrying out differential chromatography by simultaneously introducing samples into two parallel chromatographic columns, photometrically monitoring the outflow from the columns, electronically subtracting the output of one photometer from that of the other, and plotting the difference as a function of time. The present invention differs from that of the Scott et al patent in that it employs but a single column with two detectors and utilizes a variable volume cell in conjunction with one of the detectors, all as will be described hereinafter.

Other prior art, developed in the course of a preliminary search, consists of U.S. Pat. Nos. 3,223,747; 3,458,437; 3,486,304; 3,493,497; 3,508,880; 4,032,445; 4,043,906; 4,070,284; 4,128,476 and 4,137,161.

SUMMARY OF THE INVENTION

The present invention has as its principal objective the provision of an apparatus and a method for improving the definition of the signal or signals of interest in the presence of certain types of interfering signals in chromatography. Stated another way, the invention operates to maximize the signals of interest while minimizing interfering signals. The apparatus of the invention in one embodiment thereof is essentially comprised of a chromatographic column through which a sample can be passed and a first detector, a variable volume cell and a second detector connected to the output of the column. The detectors and variable volume cell are connected together in series in the order listed. The apparatus also includes means for recording the differential output of the detectors. By passing the sample sequentially through the detectors and adjusting the volume of the variable volume cell, the interfering components can be made to be present in both detectors whereby partial cancellation occurs and the signal of interest becomes more readily detectable.

In another embodiment of the invention, where detection is accompanied by destruction of the sample, means are provided to split the outflow of the column and one resultant portion of the outflow goes directly to a first detector and the other portion goes to a variable volume cell and a second detector connected in series. As with the modification described just above, by adjusting the volume of the cell the interfering components can be made to appear in both detectors whereby partial cancellation occurs.

BRIEF DESCRIPTION OF THE DRAWINGS

FIG. 4 is an illustration of another embodiment of the invention;

FIG. 7A is a chromatogram produced by the apparatus of FIG. 1 there being no interfering signal at the peak of interest;

FIGS. 7B, 7C and 7D are chromatograms produced by the apparatus of the invention while varying the volume of the variable volume cell.

DESCRIPTION OF THE PREFERRED EMBODIMENTS

Figure 1:
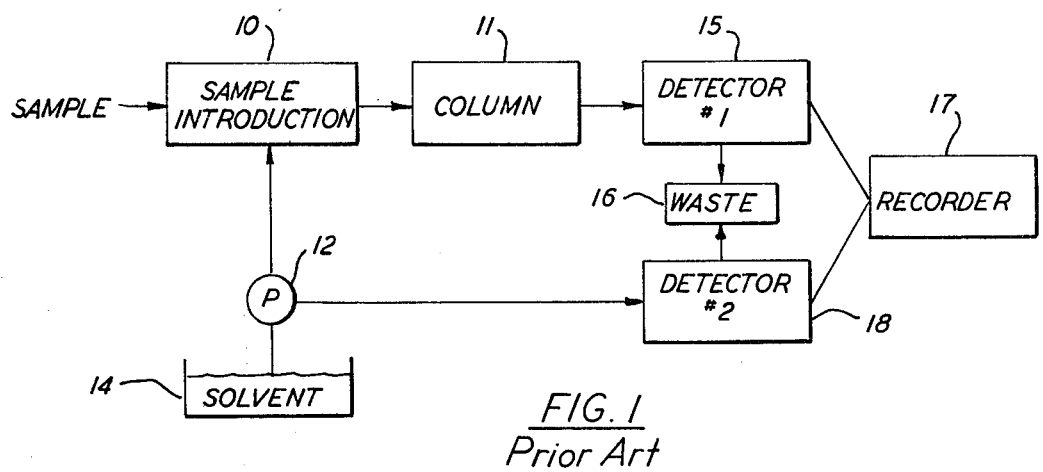
FIG. 1 is a diagrammatic illustration in the form of a flow chart of a prior art chromatographic apparatus.
Figure 2:
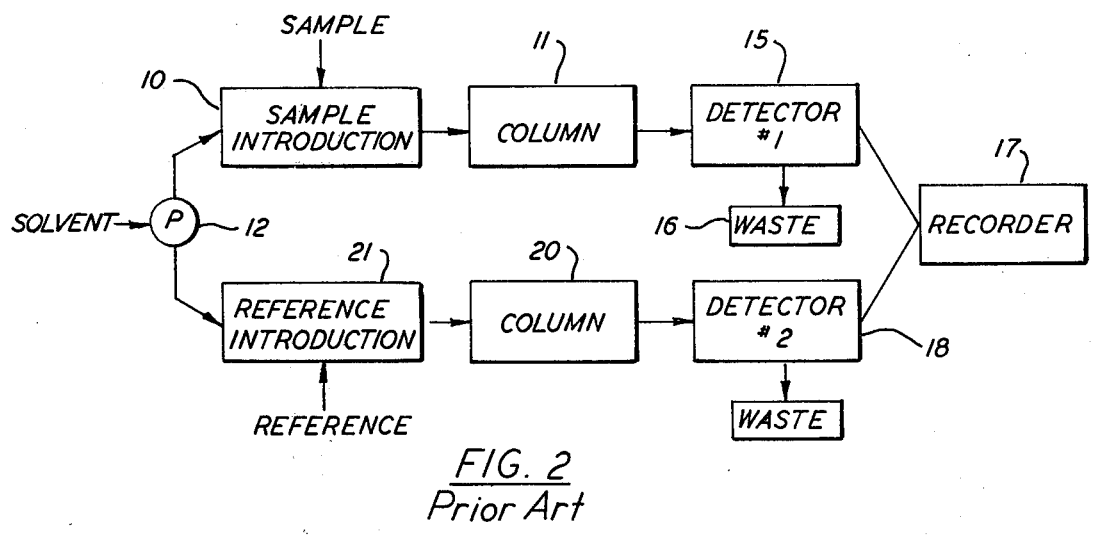
FIG. 2 is an illustration similar to FIG. 1 of another prior art apparatus.

Reference is now made to the drawings, and in particular, to FIGS. 1 and 2 illustrating prior art chromatographic apparatus. In FIG. 1, the sample, which may contain unknown components, is mixed with a suitable solvent as indicated at 10 and the resulting solution or eluate is introduced under pressure into a chromatographic column 11. The solvent is normally delivered to the column by a pump 12 which brings the solvent from a reservoir 14 or other source. The column 11 can be any one of a number of types whose constructions are well known in the art.

Figure 5:
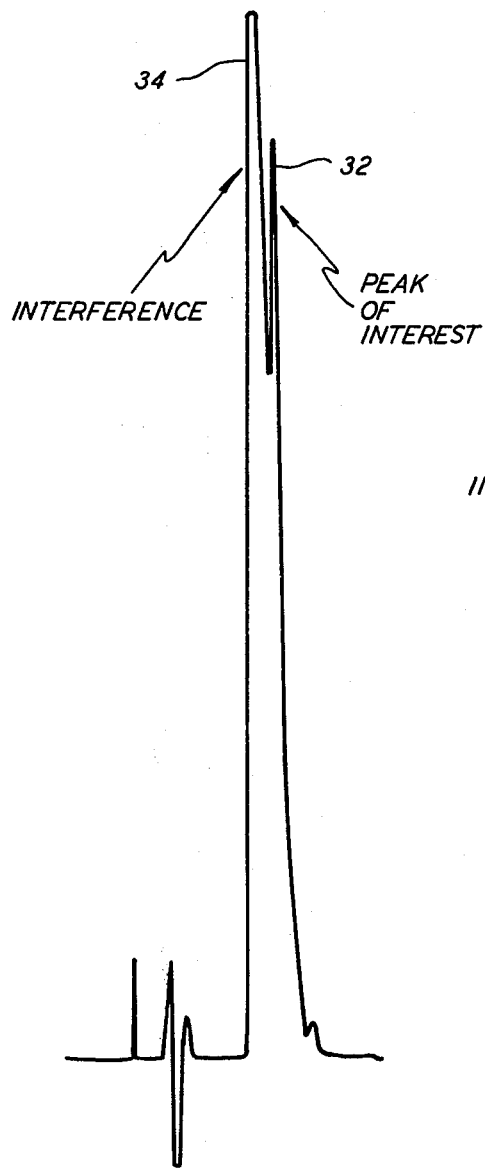
FIG. 5 is a chromatogram produced by the apparatus of FIG. 1 showing the effect of a broad band interference on a peak of interest.

The outflow from the column passes through a known type of detector 15, as for example a photometric detector, and from thence to waste as indicated at 16. The output from the detector is recorded by a recording device 17 of a known type and the resultant chromatogram may be as shown by FIG. 7A if no interfering signals are present, or as shown by FIG. 5 if there are interfering signals.

Since the carrier solvent may itself have impurities or may vary in composition, it is advantageous to pump some of the solvent through a second detector 18 and when this is done the recording device records the difference in the detector outputs. This provides a more accurate chromatogram of the sample.

FIG. 2 illustrates another prior art arrangement wherein the unknown sample is compared with a reference having known components, one of which is the solvent. In this arrangement, the upper part or branch of the apparatus is the same as that of FIG. 1. The solvent is pumped through two parallel lines to column 11 and an identical second column 20 with the sample being added to the solvent at 10 and the reference being added to the solvent at 21. The resulting sample and reference solutions are simultaneously introduced under pressure into the columns 11 and 20.

The outflow from the columns 11 and 20 simultaneously pass through the detectors 15 and 18 respectively and the difference in the detector outputs is recorded by the recording device 17. The chromatographic apparatus of FIG. 2 is quite similar to that disclosed in U.S. Pat. No. 3,847,550 discussed above.

Figure 3:
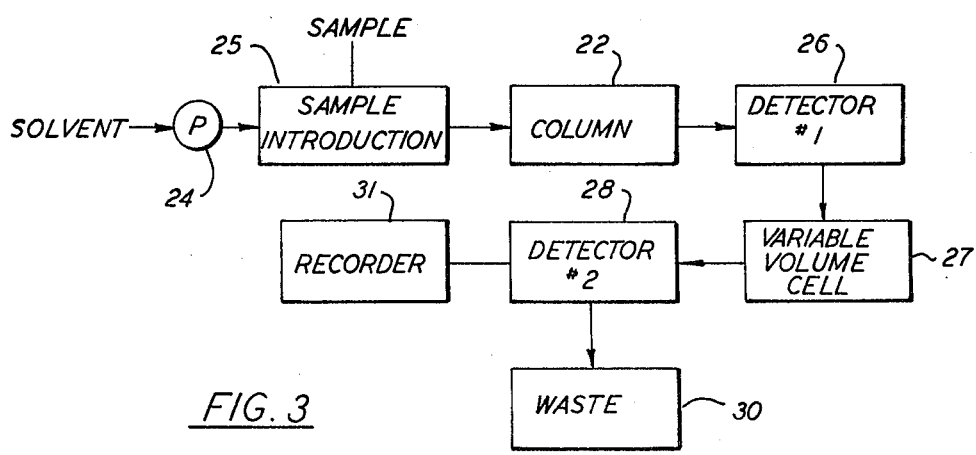
FIG. 3 is an illustration similar to FIG. 1 but showing chromatographic apparatus embodying the present invention.

Referring now to FIG. 3 showing an apparatus embodying the invention, it may be seen that the components of the apparatus are in a series arrangement as compared with the parallel arrangement of FIG. 2. Thus, a suitable solvent is delivered under pressure to a conventional chromatographic column 22 by a pump 24 with the sample being introduced into the solvent at 25. In accord with the invention, the outflow from the column passes through a first detector 26, a variable volume cell 27 and a second detector 28, the detectors being identical and of a well known, commercially available type. From the second detector 28, the column outflow passes to waste as indicated at 30.

Figure 8:
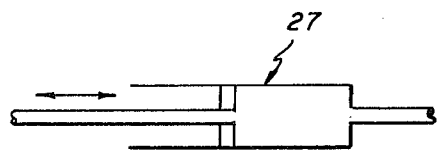
FIG. 8 is a diagrammatic illustration of one form of a variable volume cell used in the apparatus of the invention.

The variable volume cell 27 can be any suitable receptacle or vessel whose volume can be varied while passing a fluid through it. The volume can be varied by means of a piston or syringe type of arrangement as shown diagrammatically in FIG. 8, or by telescoping tubular members or the like.

A known type of recording device 31 also forms a part of the FIG. 3 apparatus and this is operable to record the difference in the outputs of the first and second detectors 26, 28. With the apparatus just described, if the signal or peak of interest is superimposed upon a broad band interference signal, the volume of the variable volume cell 27 can be adjusted so as to cause the interfering components to be present in both detectors whereby partial cancellation occurs and the signal of interest becomes more readily detectable.

Figure 6:
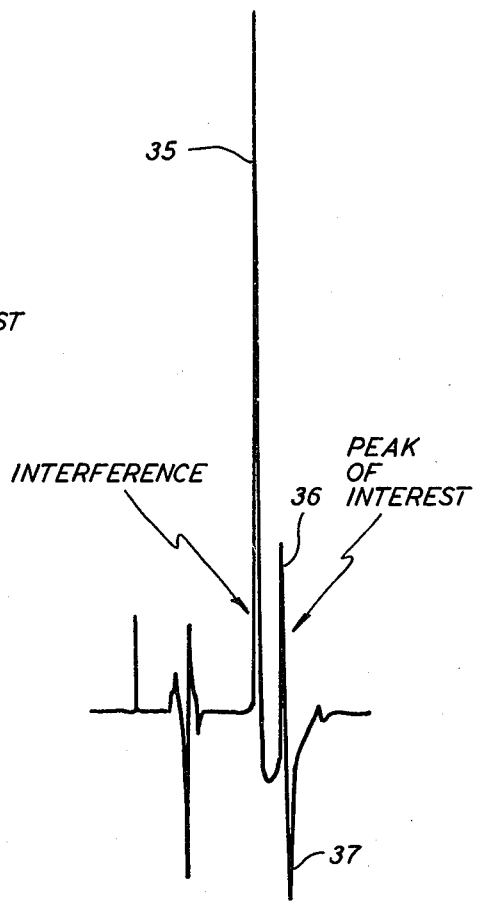
FIG. 6 is a chromatogram produced by the apparatus of the invention with the same sample as the one used for the FIG. 5 chromatograph.

To aid in understanding what the invention does, reference is made to FIGS. 5 and 6 of the drawings. FIG. 5 shows a chromatogram such as would be produced by the apparatus of FIG. 1 where a component of interest flows from the chromatographic column as a sharp band superimposed upon interfering components flowing from the column as a broad band. Thus, the recording device would record the output of the detector as a sharp peak of interest 32 superimposed on a broader interference peak 34, and it would be difficult to apportion the overall peak between the signal of interest and the interfering signals.

FIG. 6 shows a chromatogram such as would be produced by the apparatus of the invention, FIG. 3, with a sample identical to that which produced the FIG. 5 chromatogram and with the variable volume cell 27 adjusted to minimize the effect of the interfering signals. Proper adjustment of the cell causes the interfering components to be present in both detectors 26 and 28 at the same time while essentially all of the component of interest is present in detector 26. This will cause partial cancellation of the interfering components and result in an interference peak 35 that is sharper and lower than that of FIG. 5. At substantially the same time, the component of interest will show on the chromatogram as a sharp peak of interest 36.

As the component of interest moves from the first detector 26 to the second one 28, a peak 37 will appear on the chromatogram opposite in sign to the peak 36. The peak to trough height of these opposite peaks of interest reflects the concentration of the component of interest which could not be ascertained from the FIG. 5 chromatogram.

Reference is now made to FIGS. 7A-7D inclusive which provide a simplified explanation of the operation of the series connected detectors and variable volume cell of the invention. First, FIG. 7A illustrates a peak of interest 38 without interfering signals, obtained by the prior art apparatus shown in FIG. 1. FIGS. 7B, C and D illustrate peaks of interest obtained by the apparatus of the invention, FIG. 3 with the volume of the variable volume cell 27 being different for each chromatogram. In these Figures, the detection of a peak of interest by the first detector 26 appears in the chromatogram as a positive peak and the detection of the same peak of interest by the second detector 28 appears as a negative peak.

If the volume of the variable colume cell is designated 'v' and that of the peaks or bands is designated 'b', then FIGS. 7B, C and D respectively represent situations where v is greater than b, v equals b and v is less than b. In FIG. 7B, baseline conditions are reached between the positive peak 40 and negative peak 41 because the sample is completely held in the variable volume cell after leaving the first detector 26. In FIG. 7C, the leading edge of the band enters the second detector 28 at the same time the trailing edge leaves the first and therefore the positive peak 43 merges smoothly with the negative peak 44. In FIG. 7D, where the cell volume is less than the band volume, the leading edge of the band enters the second detector before the trailing edge has left the first. This leads to partial cancellation of the signals and the intensity of the positive and negative peaks 45 and 46 is reduced.

In a situation such as shown in FIG. 5, where a sharp peak of interest 32 is superimposed on a broader interference peak 34, if the volume v of the variable volume cell is adjusted so that v is less than b for the broad peak and is approximately equal to b for the sharp peak, then the effect of the broad peak is minimized while leaving the sharp peak substantially unaffected as shown in FIG. 6. In the FIG. 6 situation, the baseline does not have to be defined because the concentration of the component of interest can be quantitated by the peak to trough height of the peaks 36 and 37 of interest, or by the sum of the areas of these peaks. From the foregoing, it can be seen that the variable volume cell provides an important additional parameter in chromatography and can be used in any situation where the output is represented as the differential of two detectors.

Apparatus as disclosed in FIG. 3 has been employed using a Waters HPLC (High Pressure Liquid Chromatography) equipped with a Merck RP-2 chromatographic column and an LDC Spectromonitor III ultra violet detector system set at 240 nm. The sample and reference detectors in the instrument were connected together in series with a variable volume cell in between, the cell being similar to that shown diagrammatically in FIG. 8.

FIG. 4 illustrates a modification of the apparatus of the invention for use when detection is accompanied by destruction of the sample. In such a situation the series arrangement of FIG. 3 cannot be used because the sample would be completely consumed by the first detector 26. In the FIG. 4 modification, solvent, whether liquid or gas, is delivered under pressure to a column 48 by a pump 49 or other means with the sample being introduced into the solvent at 50. The outflow from the column is delivered to a splitter device 51 which divides the outflow into two parts. From the splitter, one part of the column outflow passes to a first detector 52 and the other part passes to a variable volume cell 54 and a second detector 55. The individual components of this modification operate in the same manner as the corresponding components in the FIG. 3 modification, and the difference in the outputs of the two detectors is recorded by a recording device 56.

From the foregoing description, it will be apparent that the invention provides a novel and very advantageous apparatus and method for reducing interferences in chromatography. As will be understood by those familiar with the art, the invention may be embodied in other specific forms without departing from the spirit or essential characteristics thereof.

We claim:

1. Apparatus for the reduction of interferences in chromatography comprising in combination a chromatographic column, means for flowing a sample through the column, first and second detectors of substantially identical construction, means for delivering the ouflow from the column to the first and second detectors, variable volume cell means positioned between the column and the second detector so that the column outflow passes through the variable volume cell before entering the second detector, and means for recording the output of the detectors.

2. Apparatus as defined in claim 1 wherein the first and second detectors are in series and the variable volume cell means is positioned between the detectors, the outflow from the column being initially delivered to the first detector.

3. Apparatus as defined in claim 1 together with means connected to the column for dividing the column outlfow into two parts, one part of the outflow being delivered to the first detector and the other part thereof being delivered to the second detector through said variable volume cell means.

4. Apparatus for the reduction of interferences in chromatography comprising in combination a single chromatographic column, means for flowing a sample through the column, first and second photometric detectors of substantially identical construction, means for passing the outflow from the column through said detectors, a variable volume cell positioned between the column and the second detector whereby the column outflow passes through the cell before entering the second detector, and means for recording the differential output of the detectors.

5. Apparatus as defined in claim 4 wherein the first and second detectors are in series and the variable volume cell is positioned between the detectors, the outflow from the column being initially delivered to the first detector.

6. Apparatus as defined in claim 4 together with means connected to the column for dividing the column outflow into two parts, one part of the outflow being delivered to the first detector and the other part thereof being delivered to the second detector through said variable volume cell.

7. Apparatus for the reduction of interferences in chromatography comprising in combination a single chromatographic column; means for flowing a sample through the column; a first detector connected to the column; a variable volume cell connected to the first detector; a second detector connected to the variable volume cell; the first detector, cell and second detector being connected in series to permit the outflow from the column to pass sequentially therethrough; and means for recording the differential output of the detectors.

8. Apparatus as defined in claim 7 wherein the two detectors are photometric detectors of substantially identical construction.

9. Apparatus for the reduction of interferences in chromatography comprising in combination a single chromatographic column, means for flowing a sample through the column, means connected to the column for dividing the column outflow into two equal parts, a first detector adapted to receive one part of the column outflow, a second detector adapted to receive the other part of the column outflow, a variable volume cell connected between the dividing means and second detector whereby said other part of the column outflow passes through the cell before entering the second detector, and means for recording the differential output of the detectors.

10. Apparatus as defined in claim 9 wherein the two detectors are photometric detectors of substantially identical construction.

11. In a method of reducing interferences in chromatography wherein a sample is introduced into a solvent and the resulting solution is passed through a chromatographic column, the improvement comprising the steps of passing the outflow from the column through a first detector, a variable volume cell and a second detector, varying the volume of the variable volume cell as the column outflow is passing therethrough, and recording the difference in the output between the first and second detectors.

12. A method as defined in claim 11 together with the steps of dividing the column outflow into two parts and passing one part through the first detector and the other part through the variable volume cell and second detector.

* * * * *